United States Patent
Faull et al.

(10) Patent No.: US 6,984,657 B1
(45) Date of Patent: Jan. 10, 2006

(54) INDOLE DERIVATIVES AS MCP-1 RECEPTOR ANTAGONISTS

(75) Inventors: Alan Wellington Faull, Macclesfield (GB); Jason Grant Kettle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 100 days.

(21) Appl. No.: 10/149,101

(22) PCT Filed: Jan. 9, 2001

(86) PCT No.: PCT/GB01/00074

§ 371 (c)(1),
(2), (4) Date: Jun. 5, 2002

(87) PCT Pub. No.: WO01/51467

PCT Pub. Date: Jul. 19, 2001

(30) Foreign Application Priority Data

Jan. 13, 2000 (GB) .............................. 0000625

(51) Int. Cl.
*A61K 31/404* (2006.01)
*C07D 209/42* (2006.01)
*A61P 37/00* (2006.01)

(52) U.S. Cl. ...................................... 514/419; 548/492
(58) Field of Classification Search ................ 548/492, 548/465; 514/419
See application file for complete search history.

(56) References Cited

U.S. PATENT DOCUMENTS

| | | | |
|---|---|---|---|
| 3,557,142 A | 1/1971 | Bell | |
| 3,776,923 A | 12/1973 | Remers et al. | |
| 3,997,557 A | 12/1976 | Helsley et al. | |
| 4,529,724 A | 7/1985 | Ho | |
| 4,608,384 A | 8/1986 | Wierzbicki et al. | |
| 4,721,725 A | 1/1988 | Biller et al. | |
| 4,751,231 A | 6/1988 | Halczenko et al. | |
| 4,965,369 A | 10/1990 | Maetzel et al. | |
| 5,081,145 A | 1/1992 | Guindon et al. | |
| 5,190,968 A | 3/1993 | Gillard et al. | |
| 5,254,563 A | 10/1993 | Huth et al. | |
| 5,272,145 A | 12/1993 | Prasit et al. | |
| 5,273,980 A | 12/1993 | Frenette et al. | |
| 5,288,743 A | 2/1994 | Brooks et al. | |
| 5,290,798 A | 3/1994 | Gillard et al. | |
| 5,308,850 A | 5/1994 | Gillard et al. | |
| 5,389,650 A | 2/1995 | Frenette et al. | |
| 5,399,699 A | 3/1995 | Kolasa et al. | |
| 5,482,960 A | 1/1996 | Berryman et al. | |
| 5,684,032 A | 11/1997 | Elliott et al. | |
| 5,852,046 A | 12/1998 | Lang et al. | |
| 5,955,492 A | 9/1999 | Thompson et al. | |
| 6,184,235 B1 | 2/2001 | Connor et al. | |
| 6,337,344 B1 | 1/2002 | Defossa et al. | |
| 6,737,435 B1 * | 5/2004 | Kettle et al. ................ | 514/415 |

FOREIGN PATENT DOCUMENTS

| | | |
|---|---|---|
| DE | 298 913 A5 | 3/1992 |
| EP | 0 077 209 | 4/1983 |
| EP | 0 186 367 | 7/1986 |
| EP | 0 189 690 | 8/1986 |
| EP | 0 419 049 A1 | 3/1991 |
| EP | 0 480 659 A2 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 573 A1 | 2/1995 |
| EP | 0 822 185 | 2/1998 |

(Continued)

OTHER PUBLICATIONS

Berman, J.W. et al. Localization of Monocyte Chemoattractant Peptide-I Expression in the Central Nervous System in Experimental Autoimmune Encephalomyelitis and Trauma in the Rat. *J. Immunol.* 156, 3017–3023 (1996).

(Continued)

*Primary Examiner*—Rita Desai
*Assistant Examiner*—Robert Shiao
(74) *Attorney, Agent, or Firm*—Ropes & Gray LLP

(57) ABSTRACT

A compound of Formula I,

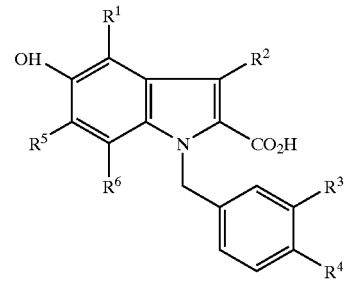

wherein: $R^1$ is hydrogen, halo, methyl, ethyl or methoxy; $R^2$ is hydrogen, halo, methyl, ethyl or methoxy; $R^3$ is a halo group, lower alkyl, lower alkenyl, lower alkynyl, alkoxy, trifluoromethyl, nitro, cyano, trifluoromethoxy, $C(O)R^7$, or $S(O)_nR^7$ where n is 0, 1 or 2 and $R^7$ is an alkyl group; $R^4$ is a halo, trifluoromethyl, methylthio, methoxy, trifluoromethoxy or lower alkyl, lower alkenyl or lower alkynyl or $COR^8$ where $R^8$ is lower alkyl; $R^6$ is hydrogen, halo, lower alkyl, lower alkenyl, lower alkynyl or $COR^9$ where $R^9$ is lower alkyl; provided that when $R^1$ is hydrogen, halo or methoxy, $R^2$ is hydrogen, halo, methyl, ethyl or methoxy, $R^5$ and $R^6$ are both hydrogen, and one of $R^3$ or $R^4$ is not halo or trifluoromethyl; or a pharmaceutically acceptable salt or prodrug thereof. These compounds have useful activity for the treatment of inflammatory disease, specifically in antagonizing an MCP-1 mediated effect in a warm-blooded animal such as a human being.

22 Claims, No Drawings

FOREIGN PATENT DOCUMENTS

| | | |
|---|---|---|
| EP | 0 275 667 | 7/1998 |
| FR | 2 565 981 | 12/1985 |
| JP | 63284177 | 11/1988 |
| JP | 4273857 | 9/1992 |
| WO | WO 86/00896 | 2/1986 |
| WO | WO 92/04343 | 3/1992 |
| WO | WO 93/12780 | 7/1993 |
| WO | WO 93/16069 | 8/1993 |
| WO | WO 93/20078 | 10/1993 |
| WO | WO 93/25546 | 12/1993 |
| WO | WO 94/14434 | 7/1994 |
| WO | WO 96/03377 | 2/1996 |
| WO | WO 96/31492 | 10/1996 |
| WO | WO 96/33171 | 10/1996 |
| WO | WO 96/37467 | 11/1996 |
| WO | WO 96/37469 | 11/1996 |
| WO | WO 97/12613 | 4/1997 |
| WO | WO 97/12615 | 4/1997 |
| WO | WO 97/30704 | 8/1997 |
| WO | WO 97/35572 | 10/1997 |
| WO | WO 98/06703 | 2/1998 |
| WO | WO 99/07351 | 2/1999 |
| WO | WO 99/07678 | 2/1999 |
| WO | WO 00/46196 * | 8/2000 |

OTHER PUBLICATIONS

Bobosik, V. & Krutosikova, A. Synthesis of N–Phenylsulfonyl Protected Furo[3,2–b]Pyyroles. *Collect. Czech. Chem. Commun.* 59, 499–502 (1994).

Dandarova, M. 13C NMR Spectra of Some Substituted Furo[3,2–b]pyrroles. *Magnetic Resonance Chem.* 28, 830–831 (1990).

Deleuran, M. et al. Localization of monocyte chemotactic and activating factor (MCAF/MCP–1) in psoriasis. *J. Dermatological Sci.* 13, 228–236 (1996).

Grimm, M.C. et al. Enhanced expression and production of monocyte chemoattractant protein–1 in inflammatory bowel disease mucosa. *J. Leukocyte Biol.* 59, 804–812 (Jun. 1996).

Harrison, C.–A. et al. Cyclopenta [b] indoles. Part 2. Model studies towards the tremorgenic mycotoxins. *J. Chem. Soc. Perkin Trans.* 1131–1136 (1995).

Hartman, G.D. & Halczenko, W. The Synthesis of 5–Alkylaminomethylthieno[2,3–b]pyrrole–5–sulfonamides. *Heterocycles* 29, 1943–1949 (1989).

Jones, M.L. et al. Potential Role of Monocyte Chemoaltractant Protein I/JE in Monocyte/Macrophage–Dependent IgA Immune Complex Alveolitis in the Rat. *J. Immunol.* 149, 2147–2154 (Sep. 15, 1992).

Kataoka, K. et al. Homopiperazines as cell migration inhibitors. *Chemical Abstracts,* Columbus Ohio, US 123, 667 (Oct. 2, 1995).

Koch, A.E. et al. Enhanced Production of Monocyte Chemoattractant Protein–1 Rheumatoid Arthritis. *J. Clin. Invest.* 90, 772–779 (Sep. 1992).

Korobehenko, L.V. et al. Synthesis and antiviral activity of pyrrolecarboxylic acids and their derivatives. *Chemical Abstracts* Columbus, Ohio, Access No.: 119:62465 (1999).

Krutosikova, A & Dandarova, M. Substituted Vinyl Azides in Synthesis of Furo[3,2–b:4,5–b]–Dipyrroles and Pyrrolo[2'3':4,5]Furo[3,2–c]Pyridines. *Heterocycles* 37, 1695–1700 (1994).

Krutosikova, A. & Dandarova, M. Reactions of Methyl 2–Formylfuro[3,2–b]pyrrole–5–carboxylates. *Chem. Papers* 50, 72–76 (1996).

Krutosikova, A. & Hanes, M. Substituted 4–Benzylfuro[3,2–b]Pyrroles. *Collect. Czech Chem.* 57, 1487–1494 (1992).

Krutosikova, A. et al. Condensed O–, N–Heterocycles by the Transformation of Azidoacrylates. *Chemical Monthly* 123, 807–815 (1992).

Krutosikova, A. et al. Derivatives of Furo[3,2–b]Pyrrole. *Collect. Czech. Chem. Commun.* 59, 473–481 (1994).

Krutosikova, A. et al. Substituted Vinyl Azides in the Synthesis of Condensed Nitrogen Heterocycles. *Chem. Papers* 48, 268–273 (1994).

Krutosikova, A. et al. Synthesis and Reactions of Furo[3,2–b]Pyrrole Type Aldehydes. *Collect. Czech. Chem. Commune.* 58, 2139–2149 (1993).

Murakami, Y. et al. Direct Regioselective Vinylation of Indoles Using Palladium (II) Chloride. *Heterocycles* 22, 1493–1496 (1984).

Rosenmund, P. et al. Decarboxylations of Some 1–Alkyl–2–carboxy–3–indolacetic Acids and Synthesis of a 5–Thiocyanato–2,3–dihydroindole. *Chem. Ber.* 108, 3538–3542 (1975)–Abstract only.

Troschutz, R. & Hoffmann, A. Synthesis of Substituted 3–Amino–4–cyano–1–oxo–1,2,5,10–tetrahy–droazepino[3,4–b]indoles. *J. Heterocyclic Chem.* 34, 1431 (1997).

Yokoyama, Y. et al. New Synthetic Method for Dehydrotryptophan Derivatives. Synthesis Studies on Indoles and Related Compounds, XXIV. *Chem. Pharm. Bull.* 42, 832–838 (1994).

Krutosikova, A. et al. Synthesis and Reactions of Furo[2,3–b]pyrroles. *Molecules* 2, 69–79 (1997).

Yokoyama, Y. et al. Palladium–Catalyzed Cross–Coupling Reaction: Direct Allylation of Aryl Bromides with Allyl Acetate. *Tetrahedron Letters* 26, 6457–6460 (1985).

* cited by examiner

INDOLE DERIVATIVES AS MCP-1 RECEPTOR ANTAGONISTS

CROSS-REFERENCE TO RELATED APPLICATIONS

This application is a national stage filing under 35 U.S.C. 371 of PCT application PCT/GB01/00074, filed Jan. 9, 2001, which claims priority from Great Britain Application No. 0000625.4, filed Jan. 13, 2000, the specifications of each of which are incorporated by reference herein.

The present invention relates to anti-inflammatory compounds that act via antagonism of the CCR2 receptor, (also known as the MCP-1 receptor), leading inter alia to inhibition of Monocyte Chemoattractant Protein-1 (MCP-1). These compounds contain an indole moiety. The invention further relates to pharmaceutical compositions containing them, processes for their preparation, intermediates useful in their preparation and to their use as therapeutic agents.

MCP-1 is a member of the chemokine family of pro-inflammatory proteins which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13, 228–236), delayed-type hypersensitivity reactions of the skin, inflammatory bowel disease (Grimm et al., 1996, *J. Leukocyte Biol.*, 59, 804–812), multiple sclerosis and brain trauma (Berman et al. 1996, *J. Immunol.*, 156, 3017–3023). An MCP-1 inhibitor may also be useful to treat stroke, reperfusion injury, ischemia, myocardial infarction and transplant rejection.

MCP-1 acts through the CCR2 receptor. MCP-2 and MCP-3 may also act, at least in part, through this receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the CCR2 receptor.

The applicants have found a class of compounds containing an indole moiety which have useful inhibitory activity against MCP-1. International Patent Application, Publication No. WO 99/07351 discloses a class of indoles with MCP-1 inhibitory activity. This application is based on the surprising discovery that particular substituted 5-hydroxy indoles are MCP-1 inhibitors which possess unexpected and beneficial properties with respect to potency and/or blood levels and/or bioavailability and/or solubility.

Accordingly, the present invention provides a compound of the formula (I):

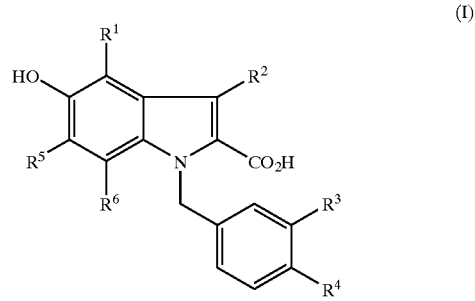

wherein:

$R^1$ is hydrogen, halo, methyl, ethyl or methoxy;

$R^2$ is hydrogen halo, methyl ethyl or methoxy;

$R^3$ is a halo group, lower alkyl, lower alkenyl lower alkynyl, alkoxy, trifluoromethyl, nitro, cyano, trifluoromethoxy, $C(O)R^7$, or $S(O)_n R^7$ where n is 0, 1 or 2 and $R^7$ is an alkyl group;

$R^4$ is a halo, trifluoromethyl, methylthio, methoxy, trifluoromethoxy or lower alkyl, lower alkenyl or lower alkynyl;

$R^5$ is hydrogen, halo, cyano, lower alkyl, lower alkenyl or lower alkynyl or $COR^8$ where $R^8$ is lower alkyl;

$R^6$ is hydrogen, halo, lower alkyl, lower alkenyl lower alkynyl or $COR^9$ where $R^9$ is lower alkyl;

provided that when $R^1$ is hydrogen, halo or methoxy, $R^2$ is hydrogen, halo, methyl, ethyl or methoxy, $R^5$ and $R^6$ are both hydrogen, and one of $R^3$ or $R^4$ is chloro, fluoro, or trifluoromethyl, then the other of $R^3$ or $R^4$ is not halo or trifluoromethyl;

or a pharmaceutically acceptable salt or prodrug thereof.

In this specification the term "alkyl" includes both straight and branched chain alkyl groups but references to individual alkyl groups such as "propyl" are for the straight chain version only. Similarly the term "alkenyl" and "alkynyl" refers to straight or branched chain unsaturated moieties. Unless otherwise stated, alkyl groups suitably contain from 1 to 10 carbon atoms, preferably from 1 to 6 carbon atoms and most preferably from 1 to 4 carbon atoms. Alkenyl and alkynyl groups suitably contain from 2 to 10 carbon atoms, preferably from 2 to 6 carbon atoms and most preferably from 2 to 4 carbon atoms. The prefix "lower" indicates that the group has up to 6 and preferably up to 4 carbon atoms. The term "halo" refers to fluoro, chloro, bromo and iodo.

Preferably $R^1$ is hydrogen or halo such as chloro or fluoro, and most preferably hydrogen.

Preferably $R^2$ is hydrogen or halo such as chloro or fluoro and most preferably hydrogen.

Suitable examples of $R^3$ include halo such as chloro, nitro or alkoxy such as methoxy.

In one embodiment, $R^3$ is trifluoromethyl and $R^4$ is methylthio, methoxy, trifluoromethoxy, alkyl in particular methyl or alkynyl in particular ethynyl.

Particular examples of $R^4$ are halo such as chloro, alkyl such as methyl, alkoxy such as methoxy or trifluoromethoxy.

In another preferred embodiment $R^4$ is halo such as chloro or trifluoromethyl and $R^3$ is alkyl, alkenyl, alkynyl, alkoxy, nitro, cyano, trifluoromethoxy, $C(O)R^7$, or $S(O)_n R^7$ where $R^7$ and n are as defined above, and $R^7$ in particular is methyl or ethyl.

Preferably $R^5$ is hydrogen.
Preferably $R^6$ is hydrogen.
In a preferred aspect of the invention there is provided a compound of formula (IA):

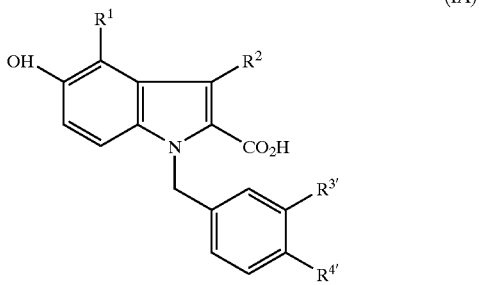

(IA)

or a pharmaceutically acceptable salt or prodrug thereof, wherein $R^1$, $R^2$ are as defined above;

$R^{3'}$ is alkyl, alkenyl, alkynyl, alkoxy, trifluoromethyl, chloro, nitro, cyano, trifluoromethoxy, $C(O)R^7$, or $S(O)_nR^7$ where $R^7$ is an alkyl group;

$R^{4'}$ is halo, methylthio, methoxy, trifluoromethoxy or methyl group;

provided that when $R^{3'}$ is trifluoromethyl, $R^{4'}$ is not trifluoromethyl or halo.

Preferably $R^1$ and $R^2$ are hydrogen.
Preferably $R^3$ is selected from methoxy, chloro or nitro.
Preferably $R^4$ is selected from chloro, methyl methoxy or trifluoromethoxy.

Preferred compounds of the invention include any one of the Examples which are illustrated in Table 1.

TABLE 1

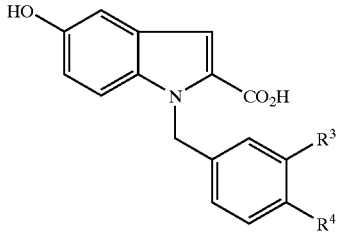

| Compound No. | $R^3$ | $R^4$ |
|---|---|---|
| 1 | OCH$_3$ | Cl |
| 2 | Cl | OCH$_3$ |
| 3 | Cl | CH$_3$ |
| 4 | NO$_2$ | CH$_3$ |
| 5 | Cl | OCF$_3$ |
| 6 | NO$_2$ | Cl |
| 7 | F | CH$_3$ |
| 8 | —C≡CH | Cl |

The invention further relates to all tautomeric forms of the compounds of formula (I).

It is also to be understood that certain compounds of the formula (I) can exist in solvated as well as unsolvated forms such as, for example, hydrated forms. It is to be understood that the invention encompasses all such solvated forms.

Compounds of formula (I) are inhibitors of monocyte chemoattractant protein-1. In addition, they appear to inhibit RANTES induced chemotaxis RANTES (Regulated upon Activation Normal T-cell Expressed and Secreted) is another chemokine from the same family as MCP-1, with a similar biological profile, but acting though the CCR1 receptor. As a result, theses compounds can be used to treat disease mediated by these agents, in particular inflammatory disease.

Suitable pharmaceutically acceptable salts of compounds of formula (I) include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a sodium salt.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include $C_{1-6}$alkyl esters, for example methyl or ethyl; $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; $C_{1-6}$alkoxycarbonyloxyethyl esters, for example 1-methoxycarbonyloxyethyl; aminocarbonylmethyl esters and mono- or di-N-($C_{1-6}$alkyl) versions thereof, for example N, N-dimethylaminocabonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include $C_{1-6}$alkanoyl esters, for example acetyl esters; and benzoyl esters wherein the phenyl group may be substituted with aminomethyl or N-substituted mono- or di-$C_{1-6}$alkyl aminomethyl, for example 4-aminomethylbenzoyl esters and 4-N,N-dimethylamiomethylbenzoyl esters.

Another aspect of the present invention provides a process for preparing a compound of formula (I) or a pharmaceuti cally acceptable salt or prodrug thereof which process comprises:

a) reacting compounds of formula (II):

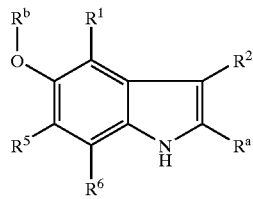

(II)

where $R^1$, $R^2$, $R^5$ and $R^6$ are as defined in relation to formula (I), $R^a$ is carboxy or a protected form thereof and $R^b$ is hydrogen or a suitable hydroxy protecting group, with a compound of formula (III):

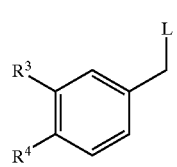

(III)

where $R^3$ and $R^4$ are as defined in relation to formula (I) and L is a displaceable group; and thereafter if necessary i) converting a compound of the formula (I) into another compound of the formula (I);
ii) removing any protecting groups; or
iii) forming a pharmaceutically acceptable salt or prodrug thereof.

Suitable values for L are for example, a halogeno or sulphonyloxy group, for example a chloro, bromo, methanesulphonyloxy or toluene-4-sulphonyloxy group.

Compounds of formula (II) and (III) are suitably reacted together in an inert organic solvent such as N,N-dimethylformamide, dichloromethane or acetonitrile in the presence of a base such as sodium hydroxide, sodium hydride or potassium carbonate. Suitably the reaction is effected in the presence of a phase transfer catalyst such as tetra-n-butylammonium hydrogensulphate. Reaction times may range for 1–6 hours preferably for 1–3 hours.

Moderate temperatures for example of 15–30° C., preferably 20–25° C. are employed.

Compounds of formula (II) may be commercially available, or they may be made by modification using known processes of commercially available compounds of formula (II). In particular, they may be prepared by reacting a compound of formula (IV):

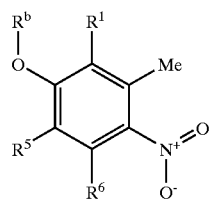

(IV)

where $R^1$, $R^5$, $R^6$ and $R^b$ is as defined above with a compound of formula (V)

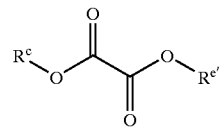

(V)

where $R^c$ and $R^{c'}$ are independently selected from $C_{1-4}$alkyl.

Compounds of formula (IV) and (V) are suitably reacted together under Reissert reaction conditions such as in an inert solvent (such as tetrahydrofuran), in the presence of a base (such as potassium ethoxide), at a temperature range of 15–30° C. preferably 20–25° C., for 10–20 hours preferably 15–17 hours. The resulting compound is isolated and dissolved in an alcohol such as ethanol and an organic acid (such as acetic acid) and a transition metal catalyst (such as 10% Pd/C) and cyclohexene is added. The mixture may then be heated at a temperature of 60–120° C. preferably at 70–90° C. for 15–25 hours preferably 16–20 hours to give a compound of formula (II) wherein $R^a$ is —$CO_2C_{1-4}$alkyl.

Alternatively, compounds of formula (II) can be prepared by reacting a compound of formula (VI):

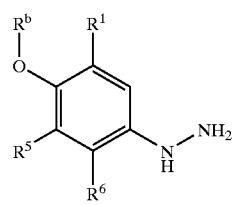

(VI)

where $R^1$, $R^5$, $R^6$ and $R^b$ are as defined above, with a compound of formula (VII):

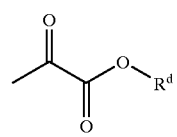

(VII)

where $R^d$ is $C_{1-4}$alkyl.

Compounds of formula (VI) and (VII) are suitably reacted together under Fischer conditions such as with an organic acid (such as acetic acid), in an alcohol (such as ethanol), at a temperature of 60–90° C., preferably 75–85° C., for 1–5 hours, preferably 1–3 hours. The resulting compound is mixed with a strong acid (such as polyphosphoric acid) and heated at 90–150° C. preferably 100–120° C., for 0.5–4 hours, preferably 0.5–2 hours to give a compound of formula (II) in which $R^2$ is hydrogen. Then, if desired, $R^2$ can be optionally converted into another value of $R^2$ as defined in formula (I) using techniques known in the literature.

In a preferred alternative, compounds of formula (II) are obtained by cyclisation of a compound of formula (VIII)

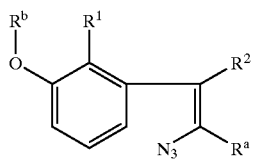

(VIII)

where $R^1$, $R^a$, $R^b$ and $R^2$ are as defined above.

Cyclisation may be effected by refluxing the compound in an organic solvent such as xylene. Compounds of formula (VIII) are suitably prepared by reacting a compound of formula (IX)

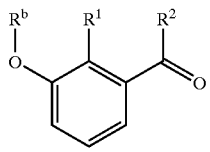

(IX)

where $R^1$, $R^2$ and $R^b$ are as defined above, with a compound of formula (X)

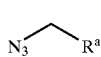

(X)

where $R^a$ is as defined above. The reaction is suitably effected in an organic solvent such as an alcohol, in particular methanol in the presence of a base such as an alkali metal alkoxide, in particular sodium methoxide. Moderate temperatures of from –30 to 20° C. are suitably employed.

Compounds of formula (III), (IV), (V), (VI), (VII), (VIII), (IX) and (X) are known or commercially available or are prepared by processes known in the art by standard manipulation of commercially available or known materials.

$R^c$ and $R^d$ are $C_{1-4}$alkyl. Preferably $R^c$ and $R^d$ are methyl or ethyl.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as carboxy or hydroxy it may be desirable to protect the group in some of the reactions mentioned herein.

A suitable protecting group or a hydroxy group is, for example, an acyl group, for example an alkanoyl group such as acetyl an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Some of the intermediates described herein may be novel, for example intermediates of the formula (II), and as such they are provided as a further feature of the invention.

When a pharmaceutically-acceptable sale of a compound of formula (I) is required, it may be obtained, for example, by reaction of said compound with the appropriate acid (which affords a physiologically acceptable anion), or with the appropriate base (which affords a physiologically acceptable cation), or by any other conventional salt formation procedure.

According to a further aspect of the invention there is provided a pharmaceutical composition which comprises a compound of the formula (I) as defined hereinbefore or a pharmaceutically acceptable salt or prodrug thereof, in association with a pharmaceutically acceptable excipient or carrier.

The compositions of the invention may be in a form suitable for oral use (for example as tablets, lozenges, bard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for inhalation by insufflation (for example as a finely divided powder) or for paternal administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid parafin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents a exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parentally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insulation may be in the form of a finely divided powder containing particles of average diameter of, for example, $30\mu$ or much less, the powder itself comprising either active ingredient alone or diluted with one or more physiologically acceptable carriers such as lactose. The powder for insulation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of MCP-1 and/or RANTES, for example, rheumatoid arthritis.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parental route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

According to a further aspect of the present invention there is provided a compound of the formula (I) or a pharmaceutically acceptable salt or prodrug thereof, as defined hereinbefore for use in a method of treatment of the human or animal body by therapy. Conveniently, the invention provides a method of treating inflammatory disease by administering a compound of formula (I) or a pharmaceutically acceptable salt or prodrug thereof or a pharmaceutical composition thereof as described above.

A further feature of the present invention is a compound of formula (I) and pharmaceutically acceptable salt or prodrug thereof, for use as a medicament.

Conveniently this is a compound of formula (I), or a pharmaceutically acceptable salt or prodrug thereof for use as a medicament for antagonising an MCP-1 (and/or RANTES) mediated effect in a warm-blooded animal such as a human being.

Thus according to a further aspect of the invention there is provided the use of a compound of the formula (I), or a pharmaceutically acceptable salt or prodrug thereof, in the manufacture of a medicament for use in antagonising an MCP-1 (and/or RANTES) mediated effect in a warm-blooded animal such as a human being.

According to a further feature of the invention there is provided a method of antagonising an MCP-1 (and/or RANTES) mediated effect in a warm-blooded animal, such as a human being, in need of such treatment which comprises administering to said animal an effective amount of a compound of formula (I) or a pharmaceutically acceptable salt or prodrug thereon as defined hereinbefore.

Biological Testing.

The following biological test methods, data and Examples serve to illustrate the present invention.

Abbreviations:

| | |
|---|---|
| ATCC | American Type Culture Collection, Rockville, USA. |
| BCA | Bicinchroninic acid, (used, with copper sulphate, to assay protein) |
| BSA | Bovine Serum Albumin |
| DMEM | Dulbecco's modified Eagle's medium |
| EGTA | Ethylenebis(oxyethylenenitrilo)tetraacetic acid |
| FCS | Foetal calf serum |
| HEPES | (N-[2-Hydroxyethyl]piperazine-N'-[2-ethanesulphonic acid]) |
| HBSS | Hank's Balanced Salt Solution |
| hMCP-1 | Human Monocyte Chemoattractant Protein-1 |
| PBS | Phosphate buffered saline |
| PCR | Polymerase chain reaction |

AMPLITAQ™ available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 72 with 1 M NaOH.

Non-Essential Amino Acids (100× concentrate) is: L-Alanine, 890 mg/l L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 μg/mL.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.*, 1949, 71, 196.

Synthetic cell culture medium, RPMI 1640 was obtained from Gibco; it contains inorganic salts [$Ca(NO_3)_2.4H_2O$ 100 mg/l; KCl 400 mg/l; $MgSO_4.7H_2O$ 100 mg/l; NaCl 6000 mg/l; $NaHCO_3$ 2000 mg/l & $Na_2HPO_4$ (anhyd) 800 mg/l)], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

Blood Sedimentation Buffer contains 8.5 g/l NaCl and 10 g/l hydroxyethyl cellulose.

Lysis Buffer is 0.15 M $NH_4CT$, 10 mM $KHCO_3$, 1 mM EDTA

Whole Cell Binding Buffer is 50 mM HEPES, 1 mM $CaCl_2$, 5 mM $MgCl_2$, 0.5% BSA, 0.01% $NaN_3$, adjusted to pH 7.2 with 1M NaOH.

Wash buffer is 50 mM HEPES 1 mM $CaCl_2$, 5 mM $MgCl_2$, 0.5% heat inactivated FCS, 0.5 M NaCl adjusted to pH 7.2 with 1M NaOH.

General molecular biology procedures can be followed from any of the methods described in "Molecular Cloning—Laboratory Manual" Second Edition, Sambrook, Fritsch and Maniatis (Cold Spring Harbor Laboratory, 1989).

i) Cloning and Expression of hMCP-1 Receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA*, 91, 2752). The resulting PCR products were cloned into vector PCR-II™ (In Vitrogen, San Diego, Calif.). Error free CCR2B cDNA was subcloned as a Hind III-Not I fragment into the eukaryotic expression vector pCNA3 (In Vitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR2B) was identified as the highest MCP-1 receptor B expresser.

ii) Preparation of Membrane Fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem*, 265, 19658). Protein concentration was estimated by BCA protein assay (Pierce, Rockford, Ill.) according to the manufacture's instructions.

iii) Assay $^{125}I$ MCP-1 was prepared using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, varying amounts of $^{125}I$-labeled MCP-1 were added to 7 μg of purified CHO-CCR2B cell membranes in 100 μl of Binding Buffer. After 1 hour incubation at room temperature the binding reaction mixtures were filtered and washed 5 times through a plate washer (Brandel MLR-96T Cell Harvester) using ice to cold Binding Buffer. Filter mats (Brandel GF/B) were pre-soaked for 60 minutes in 0.3% polyethylenimine prior to use. Following filtration individual filters were separated into 3.5 ml tubes (Sarstedt No. 55.484) and bound $^{125}I$-labeled MCP-1 was determined (LKB 1277 Gammamaster). Cold competition studies were performed as above using 100 pM $^{125}I$-labeled MCP-1 in the presence of varying concentrations of unlabeled MCP-1. Non-specific binding was determined by the inclusion of a 200-fold molar excess of unlabeled MCP-1 in the reaction.

Ligand binding studies with membrane fragments prepared from CHO-CCR2B cells showed that the CCR2B receptor was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 µl) were tested in competition with 100 pM labelled MCP-1 over a concentration range (0.01–50 µM) in duplicate using eight point dose-response curves and $IC_{50}$ concentrations were calculated.

Compounds tested of the present invention had $IC_{50}$ values of 50 µM or less in the hMCP-1 receptor binding assay described herein.

b) MCP-1 mediated calcium flux in THP-1 cells

The human monocytic cell line THP-1 was grown in a synthetic cell structure medium RPMI 1640 supplemented with 10% foetal calf serum, 6 mM glutamine and Penicillin-Streptomycin (at 50 µg streptomycin/ml, Gibco BRL). THP-1 cells were washed in HBSS (lacking $Ca^{2+}$ and $Mg^{2+}$)+1 mg/ml BSA and resuspended in the same buffer at a density of $3\times10^6$ cells/ml. The cells were then loaded with 1 mM FURA-2/AM for 30 min at 37° C., washed twice in HBSS, and resuspended at $1\times10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. $[Ca^{2+}]i$ was measured by excitation at 340 nm and 380 nm alternatively and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i = K_d \frac{(R - R\min)}{(R\max - R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence value at 380 nm excitation determined at $R_{min}$ and $R_{max}$, respectively.

Stimulation of THP-1 cells with hMCP-1 induced a rapid, transient rise in $[Ca^{2+}]i$ in a specific and dose dependant manner. Dose response curves indicated an approximate $EC_{50}$ of 2 nm. Test compounds dissovled in DMSO (10 µl) were assayed for inhibition of calcium release by adding them to the cell suspension 10 sec prior to ligand addition and measuring the reduction in the transmit rise in $[Ca^{2+}]i$. Test compounds were also checked for lack of agonist activity by addition in place of hMCP-1.

c) hMCP-1 and RANTES mediated chemotaxis.

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtitre plate which forms the lower well of a chemotaxis chamber fitted with a PVP-free 5 µm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with $Ca^{2+}$ and $Mg^{2+}$ without Phenol Red (Gibco) plus 0.1% BSA. Each dilution was degassed under vacuum for 30 min and was placed (400 µl) in the lower wells of the chamber and THP-1 cells ($5\times10^5$ in 100 µl RPMI 1640+0.5% BSA) were incubated in each well of the upper chamber. For the inhibition of chemotaxis the chemoattractant was kept at a constant submaximal concentration determined previously (1 nM MCP-1) and added to the lower well together with the test compounds dissolved in DMSO (final DMSO concentration <0.05% v/v) at varying concentrations. The chamber was incubated for 2 h at 37° C. under 5% $CO_2$. The medium was removed from the upper wells which were then washed out with 200 µl physiological saline before opening the chamber, wiping dry the membrane surface and centrifuging the 96-well plate at 600 g for 5 min to harvest the cells. Supernatant (150 µl was aspirated and 10 µl of cell proliferation reagent, WST-1, {4-[3-(4-iodophenyl)-2-(4-nitrophenyl)-2H-5-tetrazolio]-1, 3-phenyl disulfonate} plus an electron coupling reagent (Boehringer Mannheim, Cat. no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated hMCP-1 induced concentration dependent cell migration with a characteristic biphasic response, maximal 0.5-1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3', 6'-bis(acetyloxy)-3-oxospiro [isobenzofuran-1(3H), 9'-[9H]xanthene]-2', 7'-diyl]bis (methylene)]bis[N-[2-[(acetyloxy)methoxy]-2-oxoethyl]]-bis[(acetyloxy)methyl]ester; Molecular Probes) for 45 minutes in the dark. Cells are harvested by centrifugation and resuspended in HBSS (without Phenol Red) with $Ca^{2+}$, $Mg^{2+}$ and 0.1% BSA. 50 µl ($2\times105$ cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significance tests can be calculated. In addition to MCP-1 induced chemotaxis, this alternative form of the assay was also used to measure inhibition of RANTES (2 nm) induced chemotaxis.

d) Binding to Human Peripheral Blood Mononuclear Cells (PBMCs)

i) Preparation of Human PBMCs

Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RPMI/BSA (1 mg/ml) and 4×5 mls of cells were carefully layered over 4×5 mls of Lymphoprepa (Nycomed) in 15 ml centrifuge tubes. Tubes were spun at 1700 rpm for 30 minutes (Sorvall RT6000D) and the resultant layer of cells was removed and transformed to 50 ml Falcon tubes. The cells were washed twice in Lysis Buffer to remove any remaining red blood cells followed by 2 washes in RPMI/BSA. Cells were resuspended in 5 mls of Binding Buffer. Cell number was measured on a Coulter counter and additional binding buffer was added to give a final concentration of $125 \times 10^7$ PBMCs/ml.

ii) Assay

[$^{125}$I]MCP-1 was prepared using Bolton and Hunter conjugation (Bolton et al, 1973, *Biochem J.* 133, 529; Amersham International plc]. Equilibrium binding assays were carried out using the method of Ernst et al., 1994, *J. Immunol.*, 152, 3541. Briefly, 50 µl of $^{125}$I-labeled MCP-1 (final concentration 100 pM) was added to 40 µl (5×10$^5$ cells) of cell suspension in a 96 well plate. Compounds, diluted in Whole Cell Binding Buffer from a stock solution of 10 mM in DMSO were added in a final volume of 5 µl to maintain a constant DMSO concentration in the assay of 5%. Total binding was determined in the absence of compound. Non-specific binding was defined by the addition of 5 µl cold MCP-1 to give a final assay concentration of 100 nM. Assay wells were made up to a final volume of 100 µl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I-labeled MCP-1 was determined (LKB 1277 Gammamaster).

Test compound potency was determined by assay in duplicate using six point dose-response curves and IC$_{50}$ concentrations were determined.

No physiologically unacceptable toxicity was observed at the effective dose for compounds tested of the present invention.

The invention is further illustrated, but not limited by the following Examples in which the following general procedures were used unless stated otherwise.

i) N,N-Dimethylformamide (DMF) was dried over 4 Å molecular sieves. Anhydrous tetrahydrofuran (THF) was obtained from Aldrich SURESEAL™ bottles. Other commercially available reagents and solvents were used without further purification unless otherwise stated. Organic solvent extracts were dried over anhydrous MgSO$_4$.

ii) $^1$H, $^{13}$C and $^{19}$F NMR were recorded on Bruker WM200, WM250, WM300 or WM400 instruments using DMSO-d$_6$ with Me$_4$Si or CCl$_3$F as internal standard as appropriate, unless otherwise stated. Chemical shifts are quoted in d (ppm) and peak multiplicities are designated as follows: s, singlet; d, doublet, dd, doublet of doublets; t, triplet; dt, doublet of triplets; q, quartet; m, multiplet; br, broad.

iii) Mass spectra were recorded on VG 12—12 quadrupole, VG 70–250 SE, VG ZAB 2-SE or a VG modified AEI/Kratos MS9 spectrometers.

iv) For TLC analysis, Merck precoated TLC plates (silica gel 60 F254, d=0.25 mm) were used.

v) Flash chromatography was performed on silica (Merck Kieselgel: Art 9385).

EXAMPLE 1

N-(3-methoxy-4-chlorobenzyl)-5-hydroxyindole-2-carboxylic Acid

Sodium hydroxide (2M, 1.9 ml) was added to a stirred solution of ethyl N-(3-methoxy-4-chlorobenzyl)-5-acetoxyindole-2-carboxylate (305 mg) in methanol (3 ml) and THF (3 ml). The reaction was stirred at room temperature for 18 hours. The reaction mixture was concentrated in vacuo and then diluted with water (5 ml). The solution was acidified by the addition of aqueous hydrochloric acid (2M), extracted with ethyl acetate, dried and evaporated. The residue was purified by column chromatography eluting 20%–100% ethyl acetate to give the desired product as a solid (177 mg, 70%) NMR (CD$_3$SOCD$_3$): d 3.95 (s, 3H), 5.95 (s, 2H), 6.35 (d, 1H), 6.8 (dd, 1H), 6.9 (d, 1H), 7.0 (d, 1 µl), 7.1 (s, 1H), 7.25 (d, 1H), 7.3 (d, 1H), 9.0 (s, 1H); m/z 332 (M+H$^+$).

The procedure described in the above example was repeated using the appropriate indole ester as the starting material. Thus were obtained the compounds described below.

EXAMPLE 2

N-(3-chloro-4-methoxybenzyl)-5-hydroxyindole-2-carboxylic Acid

88% yield. NMR (CD$_3$SOCD$_3$): d 3.75 (s, 3H), 5.7 (s, 2H), 6.8 (dd, 1H), 6.9–7.1 (m, 5H), 7.4 (d, 1H), 9.0 (bs, 1H); m/z 330 (M–H$^+$).

EXAMPLE 3

N-(3-chloro-4-methylbenzyl)-5-hydroxyindole-2-carboxylic Acid

63% yield; m/z 314 (M–H$^+$).

EXAMPLE 4

N-(3-nitro-4-methylbenzyl)-5-hydroxyindole-2-carboxylic Acid

5% yield; m/z 326 (M-H$^+$).

EXAMPLE 5

N-(3-chloro-4-trifluoromethoxybenzyl)-5-hydroxyindole-2-carboxylic Acid

82% yield. NMR (CD$_3$SOCD$_3$): d 5.8 (S, 2H), 6.8 (m, 1H), 6.98 (m, 2H), 7.15 (s, 1H), 7.35 (m, 2H), 7.45 (m, 1H), 9.0 (S, 1H, 12.82 (S, 1); m/z 384 (M–H$^+$).

EXAMPLE 6

N-(3-nitro-4-chlorobenzyl)-5-hydroxyindole-2-carboxylic Acid

56% yield. NMR (CD$_3$SOCD$_3$): d 5.85 (S 2H), 6.85 (dd, 1H), 6.95 (d, 1), 7.15 (M, 1H), 7.35 (d, 1H), 7.65 (d, 1H, 7.8 (d, 1H), 9.0 (S, 1H).

EXAMPLE 7

N-(3-fluoro-4-methylbenzyl)-5-hydroxyindole-2-carboxylic Acid

18% yield NMR (CD$_3$SOCD$_3$): d 5.7 (s, 2H), 6.7 (m, 3H), 6.9 (s, 10H, 7.1 (m, 3H), 7.3 (m, 1H), 9.0 (s, 1H), 12.8 (s, 1H); m/z 298 (M–H$^+$).

EXAMPLE 8

N-[(4-chloro-3-ethylphenyl)methyl]5-hydroxyindole-2-carboxylic Acid

Sodium hydroxide (2M, 1.8 ml) was added to a solution of ethyl N-[(4-chloro-3-trimethylsilylethynylphenyl)methyl]-5-acetoxyindole-2-carboxylate (0.14 g) in methanol (5 ml) and the mixture was stirred for 3 hours. The methanol was removed and the residue obtained was diluted with water (20 ml) and extracted twice with ethyl acetate (20 ml each time). The aqueous layer was acidified with aqueous hydrochloric acid (2M) and extracted with ethyl acetate (3×25 ml). The combined ethyl acetate extracts were washed with water (30 ml) and brine (30 ml) and dried (MgSO$_4$). The residue obtained on removal of the solvent was dissolved in a mixture of ethyl acetate and iso-hexane (1:1) and passed down a 5 g silica Isolute column eluting with an ethyl acetate iso-hexane mixture (1:1) to give the title compound (65 mg). NMR (CD$_3$SOCD$_3$): d 4.5 (s, 1H), 5.7 (s, 2H), 6.8 (m, 1H), 6.9 (m, 2H), 7.1 (m, 1H), 7.2 (s, 1H), 7.35 (m, 1H), 7.4 (m, 2H), 9.0 (s, 1H); m/z 324.4 (M–H).

Preparation of Starting Materials

The starting materials for the Examples above are either commercially available or are readily prepared by standard methods from known materials. For example the following reactions (Methods A–D) are illustrations but not limitations of the preparation of the starting materials used in the above reactions.

Method A

Ethyl 5-acetoxy-N-(3-methoxy-4-chlorobenzyl)indole-2-carboxylate i) Ethyl 5-hydroxyindole-2-carboxylate

Boron tribromide (64.58 g) was added dropwise to a stirred solution of ethyl 5-methoxyindole-2-carboxylate (20 g) in dichloromethane (1000 ml) at −78° C. under an atmosphere of argon. The reaction was allowed to warm to room temperature and stirred for a further 2 hours. The reaction was poured into ice/s aqueous sodium hydrogen carbonate solution with stirring and extracted with ethyl acetate. Combined organic extracts were washed with saturated aqueous sodium hydrogen carbonate solution, water, aqueous saturated sodium chloride solution and dried. The solution was concentrated in vacuo and the residue was purified by column chromatography using 0–60% diethyl ether, iso-hexane as eluent to yield product as a white solid (9.02 g, 48%). NMR: 1.31 (t, 3H), 4.29 (q, 2H), 6.79 (dd, 1H), 6.90 (dd, 1H), 7.22 (d, 1H), 8.84 (s, 1H), 11.52 (brs, 1H; m/z 206 M+H$^+$).

ii) Ethyl 5-acetoxyindole-2-carboxylate

A stirred solution of ethyl 5-hydroxyindole-2-carboxylate (7.79 g) and 4-dimethylaminopyridine (20 mg) in acetic anhydride (80 ml) was heated at 80° C. for 4 hours. The reaction was concentrated in vacuo and the residue was dissolved in ethyl acetate. Combined organic extracts were washed with hydrochloric acid (2 M), saturated aqueous sodium hydrogen carbonate solution, water, aqueous saturated sodium chloride solution and dried. The solution was concentrated in vacuo to yield the product as a yellow solid (9.39 g, 100%). NMR: 1.20 (t, 3H), 2.10 (s, 3H), 4.19 (q, 2), 6.86 (dd, 1H), 6.97 (d, 1H), 7.20 (s, 1H), 7.29 (d, 1H); m/z 248 (M+H$^+$).

iii) Ethyl 5-acetoxy-N-(3-methoxy-4-chlorobenzyl)indole-2-carboxylate

To a solution of ethyl 5-acetoxyindole-2-carboxylate (283 mg) in DMF (6 ml) was added sodium hydride (54 mg, 60% dispersion in oil). The mixture was stirred for 30 minutes, a catalytic amount of potassium iodide and a solution of 3-methoxy-4-chlorobenzyl bromide (345 mg) in DMF (2 ml) was added. The mixture was stirred for 2 hours, quenched with water and extracted with ethyl acetate. The organic extracts were dried, evaporated and the resulting gum was purified by column chromatography elutig with 20% ethyl acetate/isohexane to give the desired product as an oil which solidified on standing (310 mg, 63%). NMR (CDCl$_3$): d 1.4 (t, 3H), 2.3 (s, 3H), 3.8 (s, 3H), 4.35 (q, 2H, 5.8 (s, 2H), 6.5 (dd, 1H), 6.7 (d, 1H), 7.05 (dd, 1H), 7.2–7.4 (m, 4H); m/z 402 (M+H$^+$).

The procedures described in Method A i)–iii) were repeated using the appropriate benzyl halide. Thus were obtained the compounds described below.

Ethyl N-(3-chloro-4-methoxybenzyl)-5-hydroxyindole-2-carboxylate

58% yield; m/z 402 (MH$^+$).

Ethyl N-(3-chloro-4-methylbenzyl)-5-hydroxyindole-2-carboxylate

73% yield; m/z 386 (MH$^+$).

Ethyl N-(3-nitro-4-methylbenzyl)-5-hydroxyindole-2-carboxylate

41% yield; m/z 396 (MH$^+$).

Ethyl N-(3-chloro-4-trifluoromethoxybenzyl)-5-hydroxyindole-2-carboxylate

86% yield NMR (CD$_3$SOCD$_3$): d 1.25 (t, 31), 2.25 (s, 3H), 4.25 (q, 2H), 5.85 (s, 2M), 6.95 (m, 1H), 7.1 (m, 1H), 7.39 (m, 2H), 7.45 (m, 2H), 7.6 (m, 1H; m/z 456 (MH$^+$).

Ethyl N-(3-nitro-4-chlorobenzyl)-5-hydroxyindole-2-carboxylate

55% yield NMR (CD$_3$SOCD$_3$): d 1.39 (t, 3H), 2.31 (s, 3H), 4.32 (q, 2H), 5.81 (s, 2H), 7.04–7.15 (m, 2H), 7.21–7.3 (m, 1H), 7.36–7.44 (m, 3H), 7.62 (s, 1H).

Method B

3-Methoxy-4-chlorobenzyl Bromide

(i)3-methoxy-4-chlorotoluene

To a solution of 2-chloro-5-methyl phenol (15.95 g) in acetone (200 ml) was added potassium carbonate (38 g) and dimethyl sulphate (11.7 ml). The mixture was refluxed for 3 hours and then filtered to give the desired product which was used without further purification (16.95 g, 98%). NMR (CDCl$_3$): d 2.35 (s, 3H), 3.9 (s, 3H), 6.7–6.8 (m, 2H), 7.15–7.3 (m, 1H).

(ii)3-methoxy-4-chlorobenzyl Bromide

A mixture of 3-methoxy-4-chlorotoluene (9.62 g) and N-bromosuccinimide (12.05 g) was refluxed whilst being irradiated with light using a photoflood lamp for 2 hours. The mixture was cooled, filtered and evaporated to give an oil which was purified by column chromatography eluting with diethyl ether to give the desired product as an oil (14.67 g, 95%). NMR (CDCl$_3$): d 3.9 (s, 3H), 4.45 (s, 2H), 6.9–7.0 (m, 2H), 7.3–7.4 (m, 1H).

In a similar manner but starting from 2-chloro-4-methyl phenol was prepared.

3-Chloro-4-methoxybenzyl Bromide

96% yield NMR (CDCl$_3$): d 3.9 (s, 3H), 4.45 (s, 2H), 6.9 (d, 1H), 7.25 (dd, 1H), 7.4 (d, 1H).
Method C

3-Nitro-4-chlorobenzyl Bromide

To a solution of 3-nitro-4-chlorobenzyl alcohol (4.67 g) and triphenyl phosphine (6.53 g) in dichloromethane (150 ml), cooled to 5° C. under an argon atmosphere, was added carbon tertrabromide (8.27 g). The resulting mixture was stirred at room temperature for 18 hours. The mixture was concentrated and purified by column chromatography eluting with iso-hexane rising to 20°ethyl acetate/isohexane to give the product as a yellow oil (5.39 g, 86%). NMR (CDCl$_3$): d 4.5 (s, 2H), 7.5 (s, 2H), 7.9 (s, 1H).
Method D

Ethyl N-[(4-chloro-3-trimethylsilylethynylphenyl)methyl]-5-acetoxyindole-2-carboxylate

(i) 4-chloro-3-iodobenzyl Alcohol

Borane-THF complex (10 ml) was added dropwise over 20 minutes to a solution of 4-chloro-3-iodobenzoic acid (1.4 g) in THF (25 ml). The reaction mixture was stirred for 2 hours and then cooled (ice bath) and methanol (20 ml) was added cautiously. The solvent was removed and the residue was dissolved in methanol (10 ml) and stirred with aq. 2M sodium hydroxide (10 ml) for 2 hours. Ethyl acetate (50 ml) was added and the mixture was washed with saturated aq. sodium bicarbonate solution (50 ml). The aqueous extracts were washed with ethyl acetate (2×50 ml) and the combined ethyl acetate extracts were washed with water (50 ml) and brine (50 ml) and died. Removal of the solvent gave 4-chloro-3-iodobenzyl alcohol (1.15 g). NMR (CD$_3$SOCD$_3$): d 4.45 (d, 2H), 5.3 (t, 1H), 7.3 (m, 1H), 7.5 (m, 1H), 7.8 (s, 1H).

(ii) 4-chloro-3-iodobenzyl Bromide

Triphenylphosphine (1.1 g) was added in portions to a solution of 4-chloro-3-iodobenzyl alcohol (1.1 g) in dichloromethane (40 ml) at 0° C. and stirring was continued for 10 minutes. Carbon tetrabromide (1.5 g) was then added in portions over 2 minutes, the reaction mixture was allowed to warm to ambient temperature and was stirred for 15 hours. The solution was added directly to a silica charged chromatography column and was eluted with dichloromethane to give 4-chloro-3-iodobenzyl bromide (1.9 g). NMR (CD$_3$SOCD$_3$): d 4.6 (s, 2H), 7.5 (m, 2H), 7.6 (s, 1H), 8.0 (m, 1H).

(iii) Ethyl N-[(4-chloro-3-iodophenyl)methyl]-5-acetoxyindole-2-carboxylate Sodium hydride (0.23 g of a 60% dispersion in oil) was added to a solution of ethyl 5-acetoxyindole-2 carboxylate (1.29 g) and tetra-n-butylammonium iodide (10 mg) in anhydrous DMF (25 ml) under a stream of argon. The reaction mixture was stirred for 15 minutes and a solution of 4-chloro-3-iodobenzyl bromide (1.9 g) in DMF (5 ml) was added. The mixture was stirred for 15 hours, then saturated aq. ammonium chloride (5 ml) was added. The residue obtained on removal of the solvent was diluted with saturated aq. ammonium chloride (50 ml) and extracted with ethyl actate (3×30 ml). The combined ethyl acetate extracts were washed with brine (100 ml) and dried. The residue obtained on removal of the solvent was purified by chromatography on silica eluting with a mixture of ethyl acetate and iso-hexane (1:9) to give the title compound (0.21 g). NMR (CD$_3$SOCD$_3$): d 1.1 (t, 3H), 2.2 (s, 3H), 4.3 (m, 2H), 5.8 (s, 2H), 6.9 (m, 1H), 7.1 (m, 1H), 7.35 (m, 1H), 7.4 (m, 2H), 7.6 (m 2H), 7.7 (m, 2H); m/z 497.5 (M+H).

(iv) Ethyl N-[(4-chloro-3-trimethylsilylethynylphenyl)methyl]-5-acetoxyindole-2-carboxylate Trimethylsilylacetylene (114 il) was added to a degassed solution of ethyl N-[(4-chloro-3-iodophenyl) methyl]-5-acetoxyindole-2-carboxylate (0.2 g), bis (triphenylphosphine)palladium (II) chloride (2 mg), triethylamine (56 il) and copper (I) iodide (1 mg) in acetonitrile and the mixture was stirred under an argon atmosphere for 12 hours. A further aliquot of bis(triphenylphosphine)palladium (II) chloride (2 mg) and trimethylsilylacetylene (114 il) was added and stirring continued for 2 hours. A further aliquot of trimethylsilylacetylene (114 il) was added and stirring was continued for 12 hours. A small amount of silica was added to the reaction mixture and the solvent was evaporated. The residue was added to a 5 g silica Isolute column and eluted with an ethyl acetate iso-hexane mixture (1:4) to give the title compound as a colourless oil (0.15 g). NMR (CD$_3$SOCD$_3$): d 0.0 (s, 9H), 1.1 (t, 31H), 2.1 (s, 3H), 4.1 (m, 2H), 5.6 (s, 2H), 6.7 (m, 2H), 6.9 (m, 2H), 7.1 (m, 1H), 7.2 (m, 2H), 7.3 (n, 1H), 7.4 (m, 1H); m/z 468.5 (M+H).

EXAMPLE 9

Pharmaceutical Compositions

This Example illustrates, but is not intended to limit, representative pharmaceutical dosage forms of the invention as defined herein (the active ingredient being termed "Compound X"), for therapeutic or prophylactic use in humans:

EXAMPLE A (a)

| Tablet I | mg/tablet |
| --- | --- |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
| --- | --- |
| Compound X | 50 |
| Lactose Ph.Eur | 223.75 |
| Croscarmellose sodium | 6.0 |

| -continued | |
|---|---|
| Maize starch | 15.0 |
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph.Eur | 93.25 |
| Croscramellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph.Eur | 488.5 |
| Magnesium | 1.5 |

(e)

| Injection I | (50 mg/ml) |
|---|---|
| Compound X | 5.0% w/v |
| 1 M Sodium hydroxide solution | 15.0% v/v |
| 0.1 M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection | to 100% |

(g)

| Injection III | (1 mg/ml buffered, to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

(h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |

| -continued | |
|---|---|
| Dichlorodifluoromethane | 1086.0 |
| Dichlorotetrafluoroethane | 191.6 |

(k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulations may comprise a compound as illustrated in Examples herein.
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:
1. A compound of the formula (I):

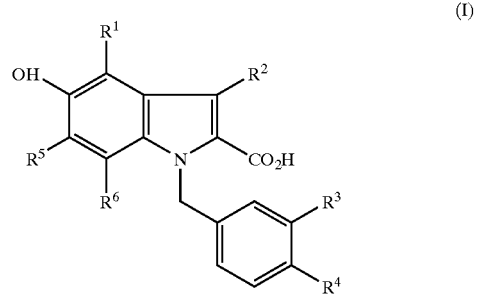

wherein:
$R^1$ is hydrogen, halo, methyl, ethyl, or methoxy;
$R^2$ is hydrogen, halo, methyl, ethyl, or methoxy;
$R^3$ is a halo group, lower alkyl, lower alkenyl, lower alkynyl, alkoxy, trifluoromethyl, nitro, cyano, trifluoromethoxy, $C(O)R^7$, or $S(O)_n R^7$ where n is 0, 1, or 2 and $R^7$ is an alkyl group;
$R^4$ is a halo, trifluoromethyl, methylthio, methoxy, trifluoromethoxy, lower alkyl, lower alkenyl, or lower alkynyl;
$R^5$ is hydrogen, halo, cyano, lower alkyl, lower alkenyl, lower alkynyl, or $COR^8$ where $R^8$ is lower alkyl; and
$R^6$ is hydrogen, halo, lower alkyl, lower alkenyl, lower alkynyl, or $COR^9$ where $R^9$ is lower alkyl;
provided that when $R^1$ is hydrogen, halo, or methoxy; $R^2$ is hydrogen, halo, methyl, ethyl, or methoxy; and $R^5$ and $R^6$ are both hydrogen; then a) when one of $R^3$ or $R^4$ is chloro, fluoro, or trifluoromethyl, then the other is not halo or trifluoromethyl; b) when one of $R^3$ or $R^4$ is chloro, the other is not methyl; and c) when $R^3$ is trifluoromethyl, $R^4$ is not methyl;

or a pharmaceutically acceptable salt or prodrug thereof.

2. A compound according to claim 1, wherein in the formula (I):
  $R^1$ is hydrogen or a halo group;
  $R^2$ is hydrogen or a halo group;
  $R^3$ is a halo group, nitro or alkoxy;
  $R^4$ is a halo group, lower alkyl, methoxy, or trifluoromethoxy; and
  $R^5$ and $R^6$ are hydrogen.

3. A compound according to claim 1, wherein in the formula (I):
  $R^1$ is hydrogen or a halo group;
  $R^2$ is hydrogen or a halo group;
  $R^3$ is trifluoromethyl;
  $R^4$ is methylthio, methoxy, trifluoromethoxy, lower alkyl or lower alkynyl; and
  $R^5$ and $R^6$ are hydrogen.

4. A compound according to claim 1, wherein in the formula (I):
  $R^1$ is hydrogen or a halo group;
  $R^2$ is hydrogen or a halo group;
  $R^3$ is lower alky, lower alkenyl, lower alkynyl, alkoxy, nitro, cyano, trifluoromethoxy, $C(O)R^7$, or $S(O)nR^7$ where n is 0, 1 or 2 and $R^7$ is an alkyl group;
  $R^4$ is a halo group or trifluoromethyl; and
  $R^5$ and $R^6$ are hydrogen.

5. A compound according to claim 1 which is a compound of the formula (IA):

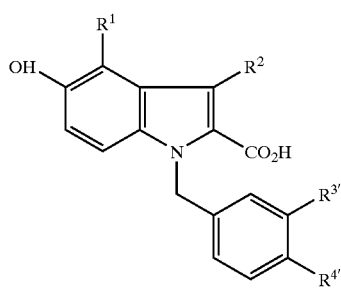

(IA)

wherein:
  $R^1$ is hydrogen, halo, methyl, ethyl, or methoxy;
  $R^2$ is hydrogen, halo, methyl, ethyl, or methoxy;
  $R^{3'}$ is chloro, lower alkyl, lower alkenyl, lower alkynyl, alkoxy, trifluoromethyl, nitro, cyano, trifluoromethoxy, $C(O)R^7$, or $S(O)nR^7$ where n is 0, 1, or 2 and $R^7$ is an alkyl group; and
  $R^{4'}$ is a halo group, methylthio, methoxy, trifluoromethoxy, or methyl;
  provided that when $R^{3'}$ is trifluoromethyl, $R^{4'}$ is not trifluoromethyl or halo;
or a pharmaceutically acceptable salt or prodrug thereof.

6. A compound according to claim 5, wherein in the formula (IA):
  $R^1$ and $R^2$ are hydrogen;
  $R^3$ is methoxy, chloro or nitro; and
  $R^4$ is chloro, methyl, methoxy or trifluoromethoxy.

7. A compound according to claim 1 which is any of the following:
  N-(3-methoxy-4-chlorobenzyl)-5-hydroxyindole-2-carboxylic acid;
  N-(3-chloro-4-methoxybenzyl)-5-hydroxyindole-2-carboxylic acid;
  N-(3-nitro-4-methylbenzyl)-5-hydroxyindole-2-carboxylic acid;
  N-(3-chloro-4-trifluoromethoxybenzyl)-5-hydroxyindole-2-carboxylic acid;
  N-(3-nitro-4-chlorobenzyl)-5-hydroxyindole-2-carboxylic acid;
  N-(3-fluoro-4-methylbenzyl)-5-hydroxyindole-2-carboxylic acid; or
  N-[(4-chloro-3-ethynylphenyl)methyl]-5-hydroxyindole-2-carboxylic acid.

8. A process for preparing a compound according to claim 1 or a pharmaceutically acceptable salt or prodrug thereof, which process comprises:
  (a) reacting a compound of formula (II):

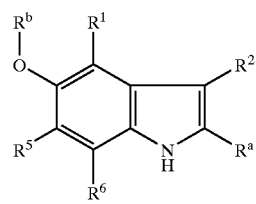

(II)

where $R^1$, $R^2$, $R^5$, and $R^6$ are as defined in claim 1;
$R^a$ is carboxy or a protected form thereof, and $R^b$ is hydrogen or a suitable hydroxyl protecting group, with a compound of formula (III):

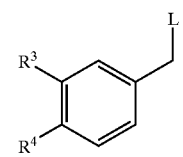

(III)

where $R^3$ and $R^4$ are defined as in claim 1; and L is a displaceable group; and optionally thereafter:
  (b) (i) converting a resulting compound of the formula (1) into another compound of the formula (I);
  (ii) removing any protecting groups; or
  (iii) forming a pharmaceutically acceptable salt or prodrug thereof.

9. A method of treating arthritis, glomerular nephritides, lung fibrosis, restinosis, alveolitis, asthma, atherosclerosis, psoriasis, hypersensitivity of the skin, inflammatory bowel disease, multiple sclerosis, brain trauma, stroke, reperfusion injury, ischemia, myocardial infarction or transplant rejection in an animal, comprising administering an effective amount of the compound according to any one of claims 1 to 7 or a pharmaceutically acceptable salt or prodrug thereof.

10. A pharmaceutical composition comprising a compound according to any one of claims 1 to 7 or a pharmaceutically acceptable salt or prodrug thereof, in association with a pharmaceutically acceptable excipient or carrier.

11. A method of manufacturing a medicament, comprising providing a compound according to any one of claims 1 to 7 or a pharmaceutically acceptable salt or prodrug thereof.

12. A method of treating inflammatory disease which comprises administering to a host in need of such treatment an effective amount of the compound according to any one of claims 1 to 7 or a pharmaceutically acceptable salt or prodrug thereof.

13. A method of treating inflammatory disease which comprises administering to a host in need of such treatment an effective amount of the pharmaceutical composition according to claim 10.

14. A method of treating arthritis, glomerular nephritides, lung fibrosis, restinosis, alveolitis, asthma, atherosclerosis, psoriasis, hypersensitivity of the skin, inflammatory bowel disease, multiple sclerosis, brain trauma, stroke, reperfusion injury, ischemia, myocardial infarction or transplant rejection in an animal, comprising administering an effective amount of a pharmaceutical composition according to claim 10.

15. A compound according to claim 1, wherein $R^1$ is hydrogen or halo.

16. A compound according to claim 1, wherein $R^2$ is hydrogen or halo.

17. A compound according to claim 1, wherein $R^3$ is selected from halo, nitro or alkoxy.

18. A compound according to claim 1, wherein $R^3$ is trifluoromethyl and $R^4$ is methylthio, methoxy, trifluoromethoxy, or alkynyl.

19. A compound according to claim 1, wherein $R^4$ is halo, methoxy, or trifluoromethoxy.

20. A compound according to claim 1, wherein $R^4$ is halo or trifluoromethyl and $R^3$ is alkenyl, alkynyl, alkoxy, nitro, cyano, trifluoromethoxy, $C(O)R^7$, or $S(O)_nR^7$ where $R^7$ and n are as defined in claim 1.

21. A compound according to claim 1, wherein $R^5$ is hydrogen.

22. A compound according to claim 1, wherein $R^6$ is hydrogen.

* * * * *